United States Patent [19]
Curbelo

[11] Patent Number: 6,043,884
[45] Date of Patent: Mar. 28, 2000

[54] DSP TECHNIQUE FOR PHOTOACOUSTIC SPECTROSCOPY (PAS) SAMPLE PULSE RESPONSE FOR DEPTH PROFILING

[75] Inventor: Raul Curbelo, Lexington, Mass.

[73] Assignee: Bio-Rad Laboratories, Inc., Hercules, Calif.

[21] Appl. No.: 09/123,823

[22] Filed: Jul. 28, 1998

Related U.S. Application Data

[60] Provisional application No. 60/055,131, Aug. 8, 1997.

[51] Int. Cl.[7] ........................................... G01B 9/02
[52] U.S. Cl. ............................... 356/346; 356/345
[58] Field of Search ................... 356/346, 432.7, 356/345

[56] References Cited

U.S. PATENT DOCUMENTS

| | | | |
|---|---|---|---|
| 5,036,708 | 8/1991 | Urban et al. | 73/801 |
| 5,166,749 | 11/1992 | Curbelo et al. | 356/346 |
| 5,262,635 | 11/1993 | Curbelo | 250/214 |
| 5,265,039 | 11/1993 | Curbelo et al. | 364/574 |
| 5,450,196 | 9/1995 | Turner | 356/346 |
| 5,612,784 | 3/1997 | Curbelo | 356/346 |
| 5,835,213 | 11/1998 | Curbelo | 356/346 |

FOREIGN PATENT DOCUMENTS

| | | |
|---|---|---|
| 2728452 | 6/1996 | France . |
| 2 285508 | 9/1994 | United Kingdom . |

OTHER PUBLICATIONS

Budeveska, Boiana O. et al., "Time–resolved impulse photoacoustic measurements by Step–scan FT–IR spectrometry," *Applied Spectroscopy*, vol. 50, No. 7, pp. 939–947 (1996).

Curbelo, Raul, "Digital signal processing (DSP) applications in FT–IR. Implementation examples for rapid and step scan systems," Proceedings of the Eleventh International Conference on Fourier Transform Spectroscopy, 1997, "AIP Conference Proceedings 430." Editor James A. de Haseth, pp. 74–83, 1998.

Drapcho, David L. et al., "Digital signal processing for step–scan fourier transform infrared photoacoustic spectroscopy," *Applied Spectroscopy*, vol. 51, No. 4, pp. 453–460 (1997).

Hinds International, Inc., "PEM–80™ Photoelastic Modulator Systems Catalog," 1988 (cover and introductory page, pp. 1–21).

Jiang, Eric Y. et al., "Development and applications of a photoacoustic phase theory for multilayer materials: The phase difference approach," *J. Appl. Phys.* 78(1), pp. 460–469 (1995).

Kam, P.Y., "Performance of BPSK with open–loop tanlock carrier recovery," *Electronics Letters Online* No. 19950227 (1995).

(List continued on next page.)

*Primary Examiner*—Robert H. Kim
*Assistant Examiner*—Andrew H. Lee
*Attorney, Agent, or Firm*—Townsend and Townsend and Crew LLP

[57] ABSTRACT

A technique for extracting the impulse response of a sample of interest includes corresponding measurements made with the sample of interest and a reference sample. At each of a series of steps in an FT-IR spectrometer, the sample of interest is illuminated with an excitation pulse of infrared radiation, acoustic signals having a time dependence $o_S(t)$ arising from the excitation pulse are captured, and a Fourier transform $O_S$ of $o_S(t)$ is computed. At each of a series of steps in the FT-IR spectrometer, the reference sample is illuminated with an excitation pulse of analytic radiation, acoustic signals having a time dependence $O_R(t)$ arising from the excitation pulse are captured, and a Fourier transform $O_R$ of $o_R(t)$ is computed. For each step, an inverse Fourier transform of the ratio $O_S/O_R$ is computed to provide a series of values $s(t_i)$ for a series of times $t_i$. These values $s(t_i)$ represent the impulse response $s(t)$ of the sample of interest for the mix of optical frequencies for that retardation value. Interferograms are processed to provide photoacoustic spectra.

23 Claims, 4 Drawing Sheets

OTHER PUBLICATIONS

Manning, Christopher J. et al., "Step–scanning interferometer with digital signal processing," *Applied Spectroscopy,* vol. 47, No. 9, pp. 1345–1349 (1993).

Noda, Isao et al., "A spectrometer for measuring time–resolved infrared linear dichroism induced by a small–amplitude oscillatory strain," *Applied Spectroscopy,* vol. 42, No. 2, pp. 203–216 (1988).

Tervo, Richard et al., "Analysis of digital tanlock loop with adaptive filtering," *IEEE Pacific Rim Conference on Communications, Computers and Signal Processing,* vol. 1, pp. 5–8 (1993).

DSP TECHNIQUE FOR PHOTOACOUSTIC SPECTROSCOPY (PAS) SAMPLE PULSE RESPONSE FOR DEPTH PROFILING

CROSS-REFERENCE TO RELATED APPLICATIONS

This application claims priority from U.S. Provisional Application No. 60/055,131, filed Aug. 8, 1997, of Raúl Curbelo, entitled "DSP APPLICATIONS IN FT-IR— IMPLEMENTATION EXAMPLES FOR RAPID SCAN AND STEP SCAN SYSTEMS," the disclosure of which, including all attached documents, is incorporated by reference in its entirety for all purposes.

BACKGROUND OF THE INVENTION

This application relates generally to FT-IR (Fourier transform infrared spectroscopy) and more specifically to phase-modulated (PM) photoacoustic spectroscopy (PAS) measurements.

A Fourier transform spectrometer typically includes an interferometer into which are directed an infrared beam to be analyzed and a monochromatic (laser) beam that provides a position reference. The interferometer has first and second mirrors.

Each of the input beams is split at a beamsplitter with one portion traveling a path that causes it to reflect from the first mirror and another portion traveling a path that causes it to reflect from the second mirror. The portions of each beam recombine at the beamsplitter, and the recombined beams are directed to appropriate detectors. The difference between the optical paths traveled by the first and second portions of the beams is often referred to as the retardation or retardation value.

One of the mirrors (referred to as the fixed mirror) is fixed or movable over a limited range while the other mirror (referred to as the movable mirror) is movable over a much more extensive range. In rapid scanning, the retardation is changed at a nominally constant rate over a significant range. This is typically accomplished by moving the second mirror at a nominally constant velocity. In step scanning, the retardation is changed intermittently, in relatively small steps of retardation. In some implementations, this is accomplished by stepping the movable mirror position.

The optical interference between the two beam portions causes the intensity of the monochromatic beam and each frequency component of the infrared beam to vary as a function of the component's optical frequency and the retardation. The detector output represents the superposition of these components and, when sampled at regular distance intervals, provides an interferogram whose Fourier transform yields the desired spectrum.

The monochromatic beam provides a reference signal whose zero crossings occur each time the relative position between the fixed and movable mirrors changes by an additional one quarter of the reference wavelength (i.e., for each half wavelength change of retardation). The data acquisition electronics are triggered on some or all of these zero crossings to provide regularly sampled values for the interferogram.

In a step scan interferometer, the relative position between the fixed and movable mirrors is stepped from one retardation value to the next and then held, at which point an intensity measurement is made. The sequence is then repeated until the desired interferogram has been acquired. The prior art teaches various techniques for accomplishing this under servo control. A number of approaches are disclosed in U.S. Pat. No. 5,166,749, issued Nov. 24, 1992 to Raúl Curbelo et al., for STEP SCANNING TECHNIQUE FOR INTERFEROMETER, which is incorporated by reference in its entirety for all purposes. This patent discloses an implementation of step scanning where the movable mirror is driven at a constant velocity and the "fixed" mirror is driven, using an actuator such as a piezoelectric transducer (PZT), in a sawtooth fashion over a small distance corresponding to the desired step size. The superposition of the two movements results in a stepped retardation.

In photoacoustic spectroscopy (PAS), a sample is placed in a cell with an infrared-transmissive window on one side and a microphone on the other. The sample is surrounded by a gas that does not absorb infrared radiation. A pulse of infrared radiation is directed at the sample, which absorbs the infrared radiation in accordance with the sample's infrared spectral characteristics. The absorbed infrared energy heats the sample, and the heat is transferred from the sample to the gas. This causes pressure changes in the gas, which are detected by the microphone. In a step scanning FT spectrometer, the process is repeated as the retardation in the spectrometer is stepped along a series of values.

The time dependence of the pressure changes provides information on the internal structure of the sample (e.g., a particular spectral feature at a particular depth in the sample). The output signal for each step is, in effect, a convolution of the excitation pulse shape, the sample response, and the detector (microphone) response. The sample response can be obtained by a deconvolution process, which is a computationally intensive process and normally requires that the detector response be known. Once the sample response is determined, spectra for different time delays relative to the pulse can be determined.

Step scan phase modulated (PM) PAS experiments using digital signal processing (DSP) have been previously reported [Manning93], [Drapcho97]. These works used continuous PM with one or several discrete frequencies for sample excitation. That is, the retardation is stepped back and forth using a continuous square wave (say one laser wavelength in each direction about the nominal retardation at 100–400 Hz) for a sufficient duration to allow demodulation of the periodic components. From the resulting in-phase and quadrature data of the PM at each step, interferograms were created for different rotation angles between the two components to compute spectra at effectively different delays with respect to the excitation, giving the desired depth information.

Alternative approaches were shown by [Budevska96]. The first approach uses amplitude modulation (AM) with a shutter to generate a pulse of infrared light from the interferometer at each step and collect the PAS time response. This AM method has the same limitations in pulse mode as in continuous modulation in that it modulates the total of infrared light from the interferometer. Since the average value is much larger than the interferogram signal of interest, this reduces the resulting signal to noise ratio (S/N). The AM method has the additional limitation of having a very low effective pulse power level when the pulse length is set to achieve a useful resolution of a fraction of a millisecond, resulting in even lower S/N in the output result.

The second approach uses a slow rise time (12 ms) PM step for the sample excitation, with no indication of how to obtain the sample time response. This PM method proposed does not address the removal of the system function (system impulse response).

SUMMARY OF THE INVENTION

The present invention provides techniques for efficiently and accurately extracting the impulse response of a sample of interest. This makes it possible to extract further information such as photoacoustic spectra in a step scanning Fourier transform spectrometer.

In short, the invention is able to extract the impulse response of the sample of interest, and hence generate desired further information such as time resolved spectra, without having to perform a deconvolution operation on the detected signal. Corresponding measurements are made with the sample of interest and a reference sample. Carbon black is preferred as a reference sample for those embodiments where it desired to have a reference with a known impulse response.

At each of a series of steps of the retardation in the spectrometer, the sample of interest is illuminated with an excitation pulse of analytic radiation (typically, but not necessarily infrared), acoustic signals having a time dependence $o_S(t)$ arising from the excitation pulse are captured, and a Fourier transform $O_S$ of $o_S(t)$ is computed.

Similarly, at each of a series of steps, the reference sample is illuminated with an excitation pulse of analytic radiation, acoustic signals having a time dependence $O_R(t)$ arising from the excitation pulse are captured, and a Fourier transform $O_R$ of $o_R(t)$ is computed.

For each step, an inverse Fourier transform of the ratio $O_S/O_R$ is computed to provide a series of values $s(t_i)$ for a series of times $t_i$. These values $s(t_i)$ represent the impulse response $s(t)$ of the sample of interest for the mix of optical frequencies for that retardation value.

If the corresponding value $s(t_k)$ is taken from each of a plurality of N steps, where $t_k$ represents a particular time relative to the pulse, the N values of $s(t_k)$, each taken from a different one of the N steps, provide an interferogram. Thus, the result is a set of interferograms, one for each value of k. A spectrum for a particular time $t_k$ can then be computed based on the interferogram having the respective values $s(t_k)$ for each of the plurality of N retardation values.

In some embodiments, the pulse of analytical radiation is generated by amplitude modulation (AM) after the retardation in the spectrometer has been stepped to a new value and held constant. In other embodiments, generally preferred, the pulse of analytical radiation is generated by phase modulation (PM), namely by the actual changing of the retardation itself. This can be the step from one retardation value to the next, or can be the result of changing the interferometer retardation back and forth in an oscillatory fashion about the nominal retardation value for that step. An advantageous form of excitation pulse is one having a chirp, namely a varying PM frequency over the pulse. This is effected by changing the retardation back and forth with a varying frequency over the duration of the pulse.

In some embodiments, it is preferred that the PM steps be characterized by relatively fast changes. This is advantageously effected by using an actuator having a short response time. A piezoelectric transducer (PZT) is particularly suitable, being capable of providing pulse rise times of a fraction of a millisecond.

A further understanding of the nature and advantages of the present invention may be realized by reference to the remaining portions of the specification and the drawings.

DESCRIPTION OF SPECIFIC EMBODIMENTS

Terminology

Reference is made to exciting a sample with an infrared pulse. In some usage, the term "pulse" implies a waveform that departs from an equilibrium value and then returns to the equilibrium value (e.g., rises to a maximum and then returns to a minimum). As used herein, the term "pulse" is intended in a broader sense to include signals that may include multiple local maxima and minima, as for example, a finite duration of an oscillating waveform.

Various terminologies are commonly applied to frequency-related quantities. For example, the character $\omega$ is used in different contexts to represent two different frequency-related quantities. In the continuous frequency domain f represents the frequency in cycles/second (Hz) while $\omega$ represents the angular frequency in radians/sec, with the two being related by the well known equation $\omega=2\pi f$. In the discrete frequency domain, applicable here, $\omega$ is given by $2\pi f/f_{sampling}$, and is thus expressed in radians (radians/sample).

Incorporation by Reference

The disclosures of all articles and references, including patent documents, mentioned in this application are incorporated herein by reference in their entirety for all purposes.

System Overview

Figure 1:
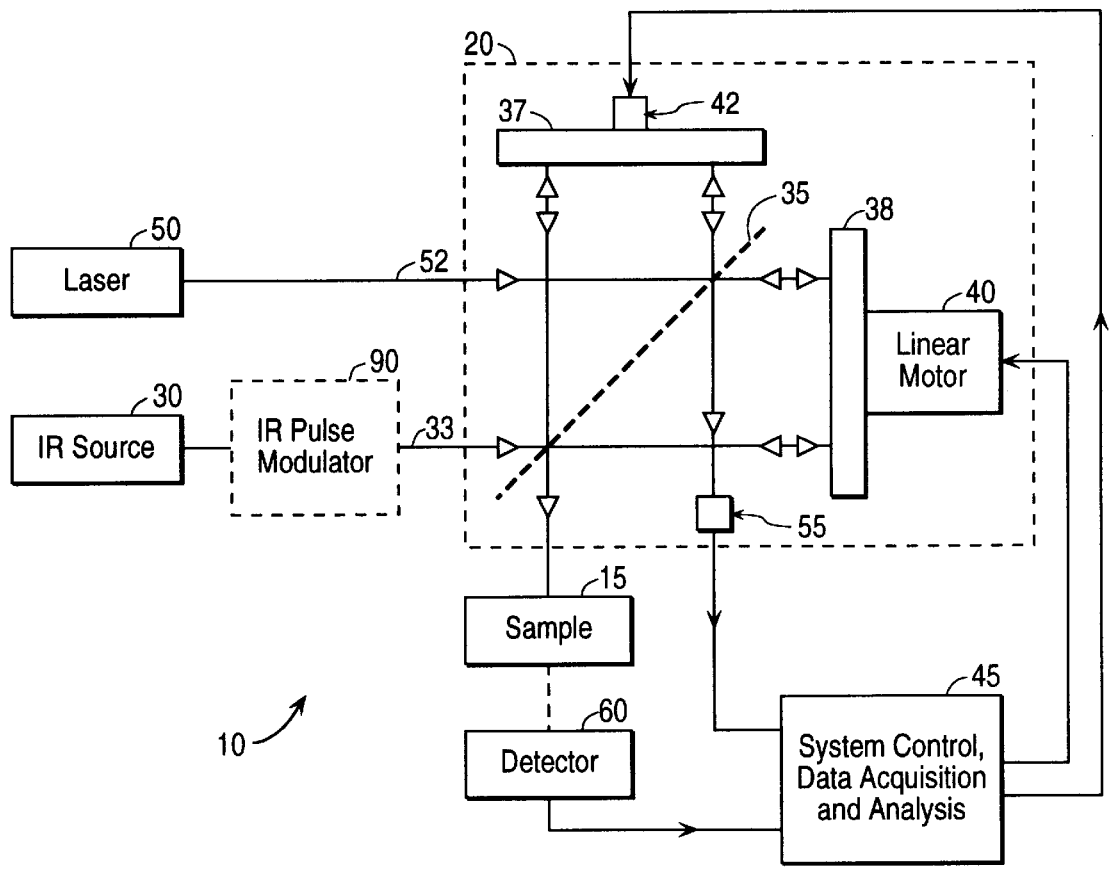
FIG. 1 is a block diagram of a Fourier transform spectrometer configured for photoacoustic spectroscopy (PAS)

FIG. 1 is a schematic view of a Fourier transform spectrometer system 10 for performing photoacoustic spectroscopy (PAS) measurements of a sample 15. Spectrometer system 10 includes a Michelson interferometer 20 and, in a typical embodiment, a broadband infrared source 30, which provides an infrared beam 32. Interferometer 20 comprises a beamsplitter 35, a fixed mirror 37, and a movable mirror 38. The two mirrors are shown at 90° to each other, but in a typical embodiment the mirrors are at 60° to each other. A linear motor 40, which may include a solenoid drive coil and an air bearing, effects large-scale movement of mirror 38. An actuator 42, preferably a piezoelectric transducer (PZT), is interposed between fixed mirror 37 and the interferometer's fixed structure (not shown), and effects small-scale movement of mirror 37.

Control, data acquisition, and data processing electronics 45 control the overall operation of the system and provide the data output required by the user. The drawing is labeled "Prior Art" since the configuration, drawn at this high level, represents known technology. The invention contemplates modifications to the data processing electronics, so that the system, with block 45 incorporating embodiments of the invention, is not prior art.

The underlying purpose of the interferometer in the spectrometer system is to modulate each frequency component of the broadband infrared beam at its own frequency as a function of retardation so that corresponding data at fixed increments of retardation provide interferogram data. Digitized interferogram data is subjected to various data manipulations, including a Fourier transform, to yield the desired spectrum. The particular data manipulations are not part of the invention, and will not be described further. A general description, however, can be found in U.S. Pat. No. 5,262,635, issued Nov. 16, 1993 to Raúl Curbelo, for TECHNIQUE FOR CORRECTING NON-LINEARITY IN A PHOTODETECTOR USING PREDEFINED CALIBRATION INFORMATION, which is incorporated by reference in its entirety for all purposes.

The system further includes a monochromatic reference system to provide signals representing fixed increments of retardation. The monochromatic reference system includes a laser 50, which provides a monochromatic beam 52 impinging on the interferometer.

Infrared beam 32 and monochromatic beam 52 are split at beamsplitter 35 with one portion of each traveling a path that causes it to reflect from fixed mirror 17 and another portion of each traveling a path that causes it to reflect from movable mirror 38. The portions of each beam recombine at beamsplitter 38, and due to optical interference between the two portions, the intensity of each frequency component of the recombined infrared beam and the intensity of the monochromatic recombined beam varies as a function of wavelength and the retardation. The recombined infrared beam is communicated to sample 15 and the recombined monochromatic beam is directed to a monochromatic detector 55. A detector 60 provides a signal representing the interaction of the recombined infrared beam with the sample.

The signal from detector 55, when conditioned by the control electronics, provides a reference signal that has a zero crossing every time the retardation changes by half the laser wavelength. The control electronics further operate to provide linear motor 40 with an appropriate voltage waveform to drive mirror 38 in the desired manner.

The drawing is simplified in that the monochromatic reference system and control electronics are also preferably configured to provide alignment corrections. To this end, there are actually three monochromatic detectors and three PZTs configured in a triangular array. Further, the monochromatic beam is broadened so that portions impinge on the interferometer over a broad enough area as to impinge on the three detectors. The three monochromatic detector signals are used by the control electronics to provide signals to the three PZTs to control the angular orientation of fixed mirror 37 and thus compensate for wobble of movable mirror 38 or systematic tilt of the movable mirror or of beamsplitter 35.

In normal FT-IR, detector 60 provides a measure of the intensity of the light that passes through, reflects from, or scatters from the sample. In PAS, detector 60 is a microphone detector (or simply microphone) that is sensitive to pressure changes in a sample cell resulting from heating of the sample.

For step scanning, which is used in the PAS measurements according to the present invention, linear motor 40 may be driven to step mirror 38 to a series of equally spaced positions with actuator 65 used merely to correct for tilts and wobble as mentioned above. However, as described above in connection with the above mentioned U.S. Pat. No. 5,166,749, step scanning can be implemented by having linear motor 40 move mirror 38 at a constant velocity and having actuator 42 drive "fixed" mirror 65 in a sawtooth fashion over a distance corresponding to the desired step size.

PAS Overview

Figure 2:
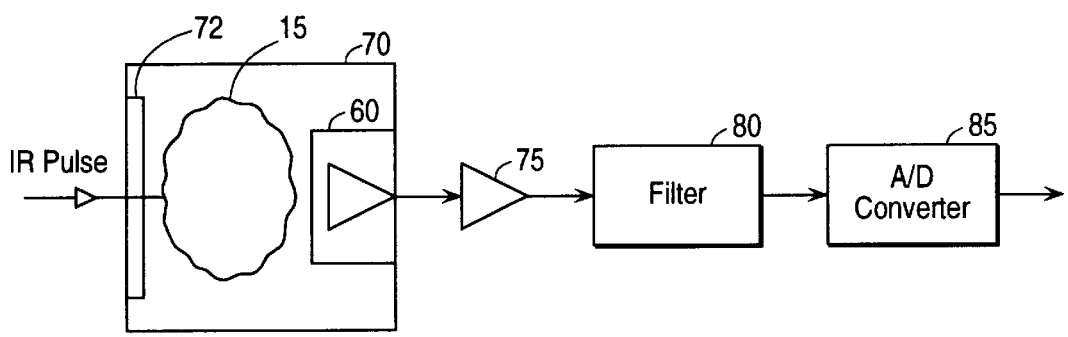
FIG. 2 is a schematic view showing a sample inside a PAS sample cell as well as the associated electronics.

FIG. 2 is a schematic view showing sample 15 inside a PAS sample cell 70. Cell 70 can be seen to have an infrared-transmissive window 72 to admit the infrared light, with microphone detector 60 mounted to one of the cell walls so as to be sensitive to changes of the internal gas pressure caused by the energy absorbed by the sample. The electrical signal from the microphone is communicated to an amplifier 75, the output signal of which is communicated to a filter 80, the bandwidth-limited output of which is communicated to an analog-to-digital (A/D) converter 85.

A/D converter 85 provides a digital signal suitable for further analysis in a general purpose computer, possibly assisted by one or more digital signal processors (also referred to as DSPs).

In PAS, the sample is subjected to an excitation pulse of IR radiation. In practice, the excitation has to be a pulse of finite duration, and in general it can be any pulse p(t). This may be implemented by having a separate IR modulator or chopper interposed in the IR beam. This is shown schematically in FIG. 1 as a block 90 (drawn in phantom). Alternatively, the pulse may be implemented by the actual stepping of the retardation [Budevska96]. That is, the PM step generated in a step scanning spectrometer can be used, especially when the rise time of the spectrometer step is short enough to provide the time resolution required. Typical rise times for an interferometer with PZTs driving a mirror are of the order of 100 $\mu$sec. The PM pulse of infrared energy that excites the sample has a time dependence designated p(t), which corresponds to the pulse p' (t) used to drive the interferometer, as modified by the transform function of the interferometer.

Figure 3:
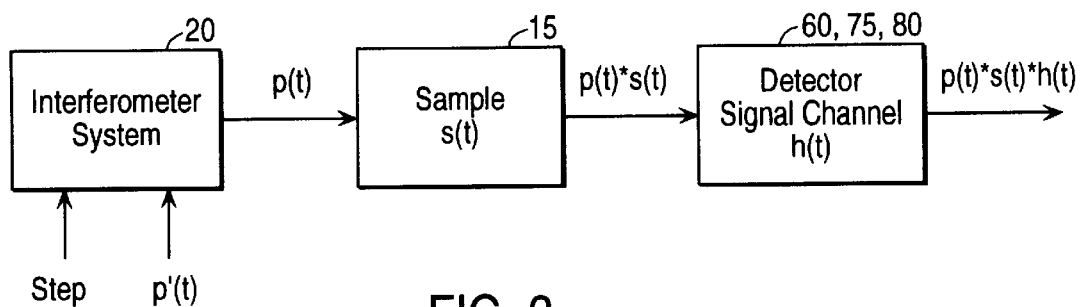
FIG. 3 is a schematic showing the output response as a function of the various input responses in a PAS measurement.

FIG. 3 is a schematic showing the output response as a function of the various input responses. The output signal o(t) for each step can be expressed as the convolution of the excitation pulse p(t), the sample impulse response s(t), and the detector system impulse response h(t). In the case of a PAS measurement, the detector system includes the PAS sample cell, its microphone, and the signal channel electronics. As will be described in greater detail below, the reference sample measurement can be used to extract the sample response from the overall response.

Data Acquisition and Analysis

The invention uses pulse PM to obtain the PAS time response of a sample to a-unit impulse. In specific embodiments, this is accomplished by performing a measurement with a reference sample whose impulse response is known. It is common practice in PAS to use carbon black as a reference material, because it has very high absorptivity across the infrared spectrum and approximates total absorption at the surface. Thus carbon black's impulse response approximates an impulse (i.e., the response to an arbitrary pulse approximates the arbitrary pulse). For the carbon black reference sample to exhibit an impulse response that approximates an impulse, it should have minimum mass. This can be accomplished by having the carbon black on a substrate that does not absorb infrared. This could be a polished aluminum block, which would reflect infrared energy that passes through the carbon black back into the carbon black. An aluminized thermal insulator could also be suitable. The reference sample should also be thermally isolated from the PAS cell.

Figure 4:
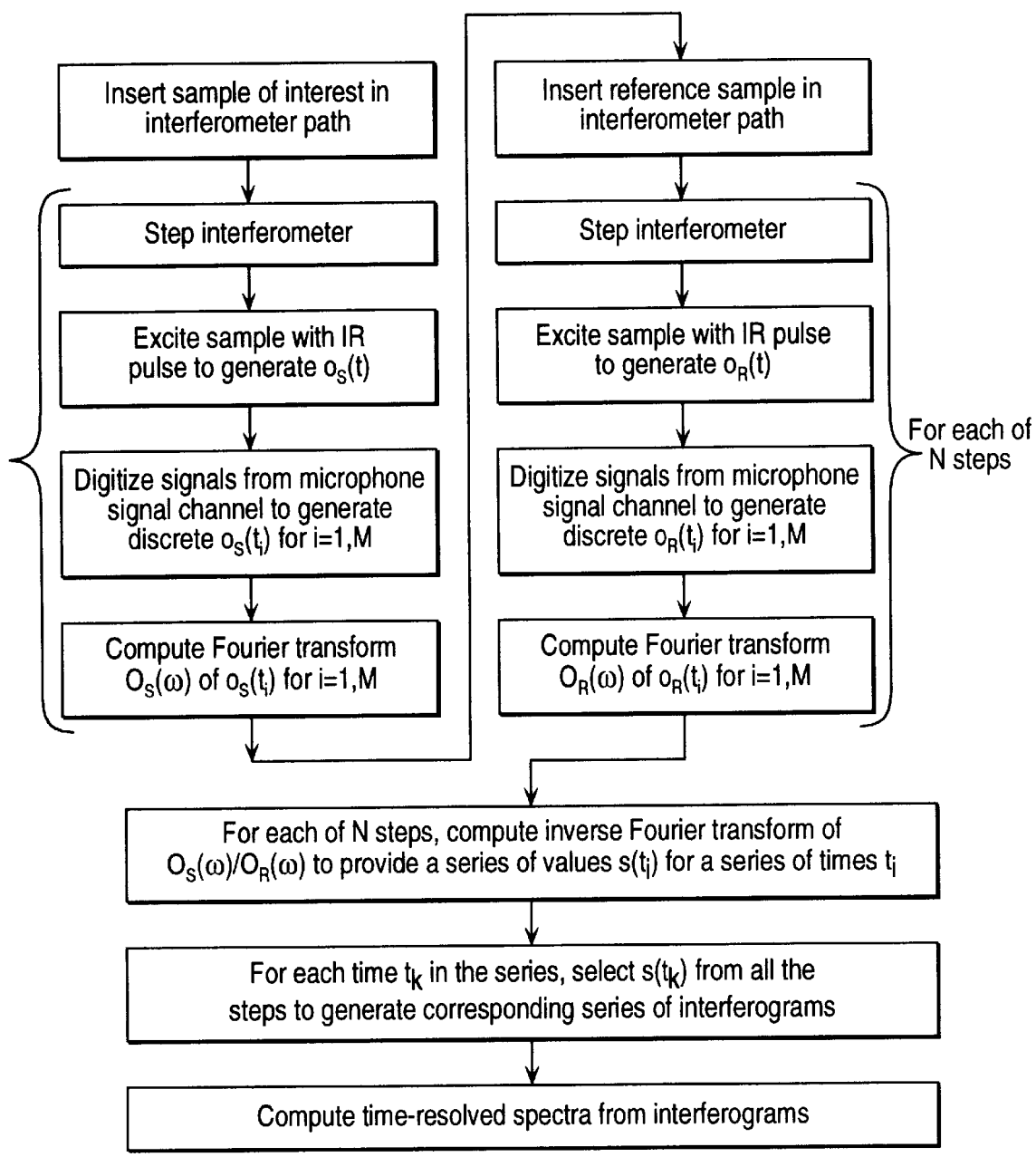
FIG. 4 is a diagram showing a sequence of steps for carrying out PAS measurements according to the invention.

FIG. 4 is a diagram showing a sequence of steps for carrying out PAS measurements according to the invention. For concreteness, the figure shows the sample of interest being measured before the reference sample. This is largely arbitrary; the order could be reversed. In principle, the measurements of the sample of interest and the reference sample could be interleaved, but this is not seen as providing sufficient benefit to outweigh the extra complication. There may be some applications, however, where it would be desirable to measure the sample of interest and the reference at a given step before proceeding to the next step. As can be seen from FIG. 4, various computations are performed on the captured digital data. These will be described in detail at this point.

For a linear time invariant system, the output $o_S(t)$ can be written as a convolution of the optical pulse time dependence p(t), the sample impulse response s(t), and the detector and signal channel response h(t) as follows:

$$o_S(t) = p(t)*s(t)*h(t) \qquad 1.$$

where the subscript S refers to the data from the sample of interest.

Equation 1 can also be rewritten by changing the order of the convolution terms as follows:

$$o_S(t) = p(t)*h(t)*s(t) \qquad 2.$$

In general none of the three terms is known. Therefore we use for a reference a sample whose impulse response s(t) approximates an impulse.

As mentioned above, carbon black is preferred as a reference sample materials because its impulse response approximates an impulse. Therefore the reference response can be equated to $u_0(t)$, the unit impulse. Applying the methodology of equations 1 and 2 to the reference sample gives:

$$o_R(t) = p(t)*h(t)*u_0(t) = p(t)*h(t) \qquad 3.$$

where the subscript R refers to the data from the reference sample.

The second part of the equation follows because the convolution with the unit impulse does not change the function. Then, substituting the right side of equation 3 into equation 2 gives:

$$o_S(t) = o_R(t)*s(t) \qquad 4.$$

For equation 4 to be valid, h(t) cannot change from the sample of interest measurement to the reference sample measurement, which requires that the PAS cell must have the same response for both cases. This can be achieved with the carbon black on a substrate whose volume is such that the reference sample volume matches the volume of the sample of interest. This ensures that the volume of gas in the cell will be the same, and therefore that the response will be the same.

Taking the Fourier transform, signified by F, of equation 4, gives the following in the frequency domain:

$$O_S(\omega) = [O_R(\omega)] \cdot [S((\omega)] \qquad 5.$$

where $$O_S(\omega) = F(o_S(t)),$$

$$O_R(\omega) = F(o_R(t)), \text{ and}$$

$$S(\omega) = F(s(t)).$$

Solving for $S(\omega)$ gives:

$$S(\omega) = O_S(\omega)/O_R(\omega) \qquad 6.$$

Taking the inverse Fourier transform, signified by $F^{-1}$, of the complex quantity $S(\omega)$ gives s(t) as follows:

$$s(t) = F^{-1}[S(\omega)] = F^{-1}[O_S(\omega)/O_R(\omega)] \qquad 7.$$

where s(t) is the sought-after impulse response of the sample for this step of the interferogram.

The result of the process above applied to each step of retardation "d" is an array I(d,t) of data from which interferograms $i_t(d)$ can be extracted.

Each of these interferograms can then be processed (apodized, Fourier transformed, phase corrected) to produce the corresponding spectra $S_t(v)$ for each desired value of "t", where t is the time delay from an equivalent impulse excitation to the sample and v is the optical frequency.

$$s_t(v) = C[i_t(d)] \qquad 8.$$

The desired result is a set of infrared photoacoustic spectra of the sample corresponding to different time delays after the excitation with an ideal impulse. For the case of a solid with uniform thermal properties and varying spectral characteristics as a function of depth, the time delays of the spectral response are related to the distance δ from the sample surface, and $S_t(v)$ is the photoacoustic spectrum of the sample at a depth δ from the surface.

The above results hold for any pulse shape. The choice of excitation pulse can be used to optimize the S/N of the result by maximizing the pulse energy distribution in the time domain of interest. As mentioned above, the excitation pulse can be generated by amplitude modulation (AM) of the beam or by phase modulation (PM). This can be by the very act of stepping the interferometer from one retardation value to the next in a series of values.

Experimental Results

Measurements were made on a laminated polymer film sample, consisting of 10-μm polyethylene (PE), on 10-μm polypropylene (PP), on 6-μm polyethylene terephthalate (PET) on an 0.25 mm polycarbonate (PC) substrate. The measurements were performed with a Bio-Rad FTS 6000 FT-IR spectrometer (Digital Division of Bio-Rad Laboratories, Inc, 237 Putnam Avenue, Cambridge, Mass. 02139) using an MTEC 300 photoacoustic detector (MTEC Photoacoustics, Inc., P. O. Box 1095 Ames, Iowa. 50014). The spectrometer was configured with a water-cooled ceramic mid-infrared source and a KBr substrate beamsplitter. Bio-Rad Win-IR Pro software, a Windows NT native application coded in Visual C++, was used to control the spectrometer. The data station was a DEC Celebris XL 5100 Pentium-based PC configured with 32 megabytes of RAM.

FIGS. 5A–5B, 6A–6B, and 7A–7B show the different functions for the data resulting from a PM step for a particular step near the centerburst of the interferogram (i.e., near zero retardation). The data were taken at a sampling rate of 5 kHz (5000 samples/sec). Although the data shown is for a single step, it is noted that a typical step rate is on the order of 2.5 Hz.

Figure 5A:
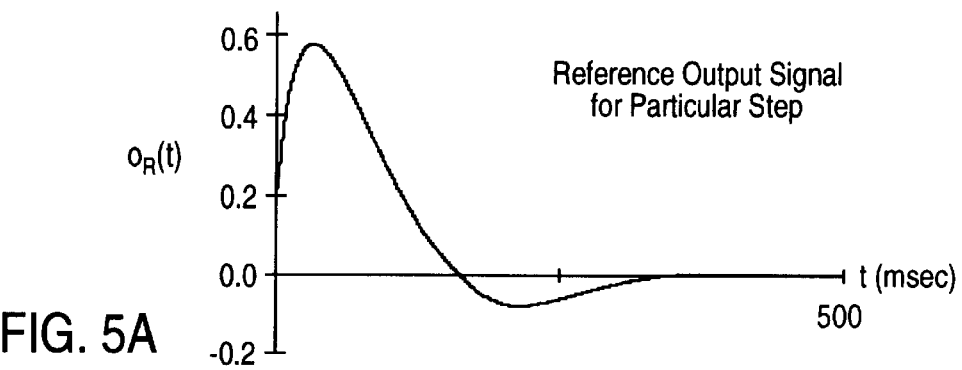
FIG. 5A shows the discrete time transient response $O_R(t)$ generated by the reference sample for a particular step.

FIG. 5A shows the discrete time transient response $o_R(t)$ generated by the reference sample for the particular step. The plot extends out to 500 ms, which corresponds to 2500 A/D samples.

Figure 5B:
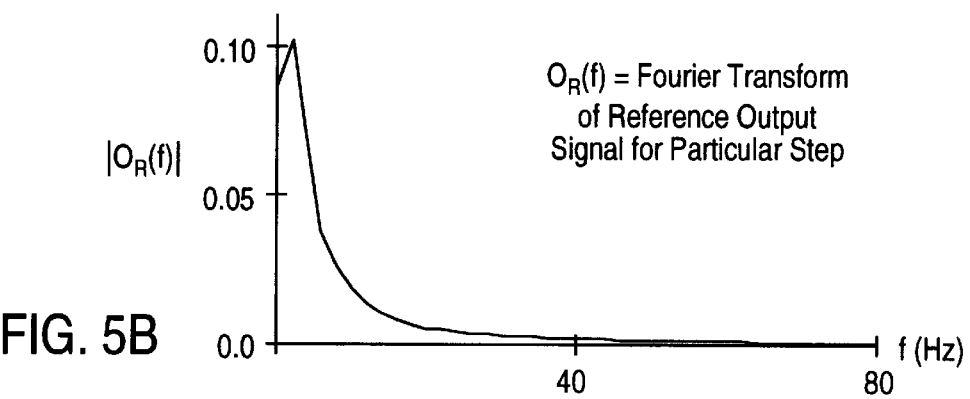
FIG. 5B shows the absolute value of the Fourier transform $O_R(f)$ of $O_R(t)$ for the particular step.

FIG. 5B shows the absolute value (magnitude) of the complex Fourier transform, $O_R(f)$, of $o_R(t)$ for the particular step. The plot extends out to 80 Hz. Although these measurements are taken in the discrete domain, the plot is shown as a function of f rather than ω since frequencies in Hz tend to be more familiar. Since ω is given by $2\pi f/f_{sampling}$, and $f_{sampling}$ is 5000 Hz, f=80 Hz corresponds to ω=0.1005 radians.

Figure 6A:
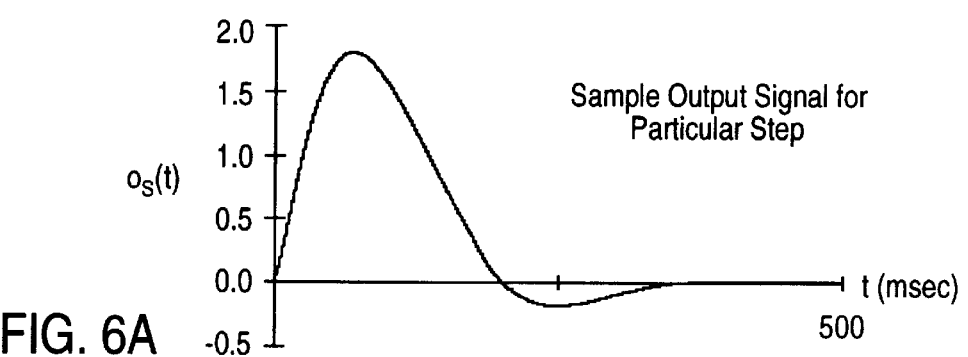
FIGS. 6A and 6B are the equivalent time transient response $O_S(t)$ and Fourier transform $O_S(f)$ for a sample of interest for the particular step.
Figure 6B:
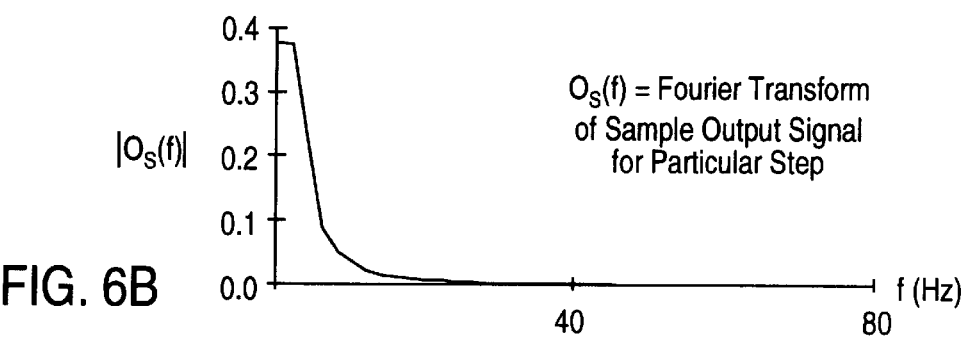

FIGS. 6A and 6B are the equivalent time transient response $o_S(t)$ and absolute value of the Fourier transform $O_S(f)$ for the sample of interest for the same particular step of the interferometer.

Figure 7A:
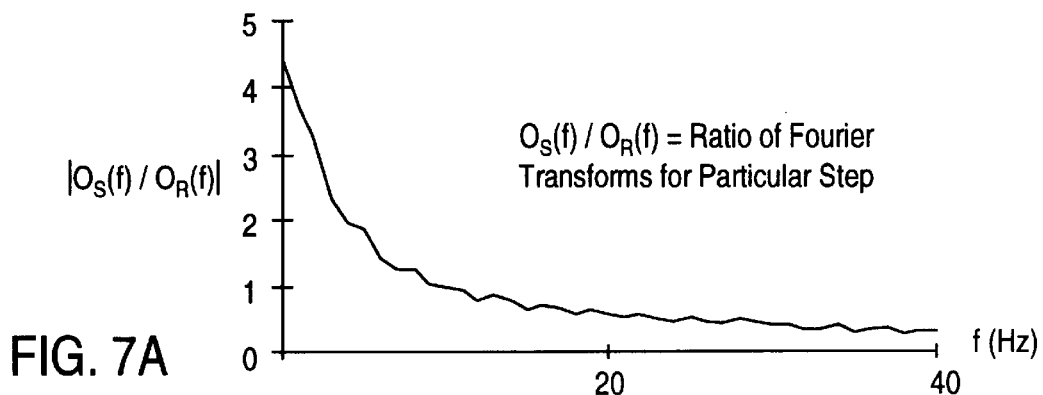
FIG. 7A shows the absolute value of the ratio of the Fourier transforms, namely $O_S(f)/O_R(f)$ for the particular step.

FIG. 7A shows the absolute value of the ratio of the complex Fourier transforms, namely $O_S(f)/O_R(f)$ for the particular step.

Figure 7B:
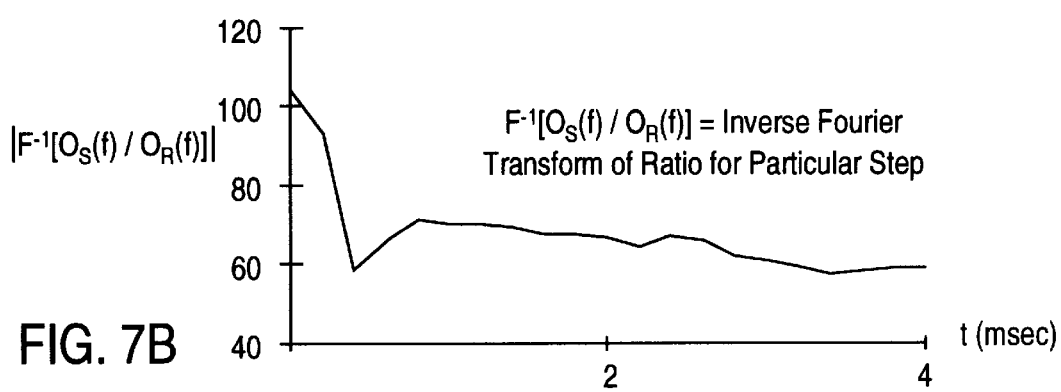
FIG. 7B shows the inverse Fourier transform of the ratio for the particular step.

FIG. 7B shows the inverse Fourier transform of the ratio. As discussed above, this yields the impulse response of the sample for the mix of optical frequencies at the retardation value that characterizes that step.

Pulse-Related Issues

The above measurements were made using the PM pulse provided by stepping the retardation. It is believed, however, that other possible generalized pulse signals would have a better spectral power distribution. Such alternative pulses include spread spectrum signals including chirps and pseudorandom unit value sequences.

Figure 8A:
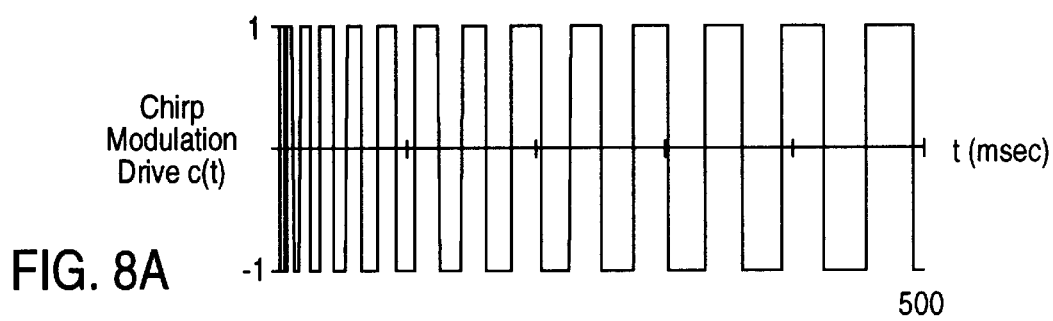
FIGS. 8A and 8B show the time profile and spectrum of a unit amplitude chirp, which can be used in accordance with the invention.
Figure 8B:
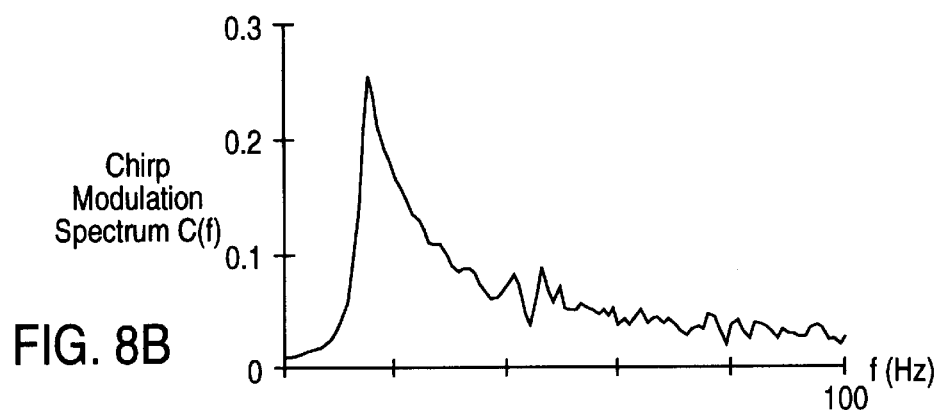

FIG. 8A shows the waveform of one example of such a pulse, namely a unit-amplitude chirp, that can be applied to step the retardation back and forth about a particular retardation. As can be seen, the retardation is stepped quickly at first, and then the rate of stepping decreases. Alternatively, the retardation could be stepped more slowly at first and more quickly later in the pulse. FIG. 8B shows the spectrum of the chirp. This provides much larger total energy for this pulse, and a much higher power density at high temporal frequencies. This will result in higher S/N for shallow depth PAS measurements.

Further, it is preferred to generate the PM pulse using the PZT to drive the fixed mirror. In prior art step scanning PAS where the linear motor is used to step the retardation by applying a step to the movable mirror, the rise time of the pulse is inherently slow. The preferred interferometer, which uses the PZT to provide the step, generates a faster rising pulse (on the order of 100 μsec as noted above). This provides higher power density at high temporal frequencies.

REFERENCES

[Budevska96] B. O. Budevska and C. J. Manning, Time-resolved Impulse Photoacoustic Measurement by Step-Scan FT-IR Spectroscopy, Applied Spectroscopy, Vol. 50, No. 7, Pages 939–947 (1996).

[Curbelo92] U.S. Pat. No. 5,166,749, issued Nov. 24, 1992 to Raúl Curbelo et al., for "Step Scanning Technique for Interferometer."

[Curbelo92] U.S. Pat. No. 5,262,635, issued Nov. 16, 1993 to Raúl Curbelo, for "Technique for Correcting Non-Linearity in a Photodetector Using Predefined Calibration Information."

[Curbelo96] U.S. patent application No. 08/712,940, filed Sep. 13, 1996 by Raúl Curbelo, for "Triple Modulation Experiment for a Fourier Transform Spectrometer."

[Curbelo97] U.S. Pat. No. 5,612,784, issued Mar. 18, 1997 to Raúl Curbelo, for "Digital Signal Processing for a FT-IR Spectrometer Using Multiple Modulations."

[Drapcho97] D. L. Drapcho, R. Curbelo, E. Y. Jiang, R. A. Crocombe, and W. J. McCarthy, Digital Signal Processing for Step-Scan Fourier Transform Infrared Photoacoustic Spectroscopy, Applied Spectroscopy, Vol. 51, No. 4, Pages 453–460 (1997).

[Jiang95] E. Y. Jiang, R. A. Palmer, and J. L Chao, Development and applications of a photoacoustic phase theory for *multilayer materials: The phase difference approach*, J. Appl. Phys. Vol. 78, No. 1, Pages 460–469 (Jul. 1, 1995).

[Manning93] C. J Manning and P. R Griffiths, Step-Scanning Interferometer with Digital Signal Processing, Applied Spectroscopy, Vol. 47, No. 9, Pages 1345–1349 (1993).

Conclusion

In conclusion, it can be seen that the present invention advances the art of photoacoustic spectroscopy (PAS). The invention allows the efficient and accurate determination of sample impulse responses and, if desired, the generation of photoacoustic spectra.

While the above is a complete description of specific embodiments of the invention, various modifications, alternative constructions, and equivalents may be used.

For example, carbon black is preferred as the reference sample since its impulse response approximates an impulse. However, other materials could be used if their impulse response were known and their spectral responses were such that the absolute value of the Fourier transform had no zeros in the frequency range of interest.

Moreover, the invention may be implemented in the context of a measurement where the reference sample is a particular instance of multiple samples of interest, and the measurement used to detect differences. Thus, while the "reference sample" would not have an impulse response that approximates an impulse, the result of dividing the Fourier transform of the sample response by the Fourier transform of the reference response would be approximately a constant for samples very much like the reference, and would show only an impulse when the inverse transform was performed. On the other hand, for a sample that differed from the reference, the result of the processing would show a qualitative difference in the impulse response.

Furthermore, while it is preferred to have the volume of the reference sample the same as that of the sample of interest, it would also be possible to calibrate for differences.

Therefore, the above description should not be taken as limiting the scope of the invention as defined by the claims.

What is claimed is:

1. A method of performing photoacoustic analysis of a sample of interest, the method comprising:

illuminating the sample of interest with a pulse of analytic radiation, the pulse having a particular time dependence p(t), detecting acoustic signals resulting from the pulse of analytic radiation encountering the sample using a detector system, capturing a series of discrete values output from the detector system, the series of discrete values having a time dependence $o_s(t)$, computing a Fourier transform $O_S$ of $o_s(t)$, illuminating a reference sample with a pulse of analytic radiation, the pulse having the time dependence of p(t), detecting acoustic signals resulting from the pulse of analytic radiation encountering the reference sample using the detector system, capturing a series of discrete values output from the detector system, the series of discrete values having a time dependence $o_R(t)$, computing a Fourier transform $O_R$ of $o_R(t)$, computing an inverse Fourier transform of the ratio $O_S/O_R$ to provide a series of values $s(t_i)$ for a series of times $t_i$, the values $s(t_i)$ representing the impulse response s(t) of the sample of interest relative to the impulse response of the reference sample.

2. The method of claim 1 wherein the reference sample has the same volume as the sample of interest.

3. The method of claim 1 wherein the reference sample has an approximate impulse response.

4. The method of claim 1 wherein the reference sample is carbon black.

5. The method of claim 1 wherein said steps on the sample of interest and the reference sample are performed in a Fourier transform spectrometer for each of a series of retardation values in the Fourier transform spectrometer.

6. The method of claim 5, and further comprising computing a spectrum for a particular time $t_k$ based on an interferogram having the respective values $s(t_k)$ for each of the N retardation values.

7. The method of claim 6 wherein said step of computing a spectrum is performed for a plurality of particular times.

8. The method of claim 5 wherein, for at least some of the retardation values, the pulse of analytic radiation is provided by stepping the retardation from a previous value to a current value in the series of retardation values.

9. The method of claim 5 wherein, for at least some of the retardation values, the pulse of analytic radiation is provided by changing the retardation in an oscillatory manner about a nominal retardation value.

10. A method of performing photoacoustic spectroscopy on a sample of interest in a Fourier transform spectrometer, the method comprising:

for each of a series of retardation values in the Fourier transform spectrometer, illuminating the sample of interest with a pulse of analytic radiation, the pulse having a particular time dependence p(t), detecting acoustic signals resulting from the pulse of analytic radiation encountering the sample using a detector system, capturing a series of discrete values output from the detector system, the series of discrete values having a time dependence $o_S(t)$, computing a Fourier transform $O_S$ of $o_S(t)$, illuminating a reference sample having a known impulse response with a pulse of analytic radiation, the pulse having the time dependence of p(t), detecting acoustic signals resulting from the pulse of analytic radiation encountering the reference sample using the detector system, capturing a series of discrete values output from the detector system, the series of discrete values having a time dependence $o_R(t)$, computing a Fourier transform $O_R$ of $o_R(t)$, computing an inverse Fourier transform of the ratio $O_S/O_R$ to provide a series of values $s(t_i)$ for a series of times $t_i$, the values $s(t_i)$ representing the impulse response s(t) of the sample of interest for that retardation value;

for at least a plurality of N retardation values, computing a spectrum for a particular time $t_k$ based on an interferogram having the respective values $s(t_k)$ for each of the N retardation values.

11. The method of claim 10 wherein said step of computing a spectrum is performed for a plurality of particular times.

12. The method of claim 10 wherein, for at least some of the retardation values, the pulse of analytic radiation is provided by stepping the retardation from a previous value to a current value in the series of retardation values.

13. The method of claim 10 wherein, for at least some of the retardation values, the pulse of analytic radiation is provided by changing the retardation in an oscillatory manner about a nominal retardation value.

14. The method of claim 13 wherein the oscillatory manner is characterized by a changing frequency to provide a chirped pulse.

15. The method of claim 10 wherein the reference sample has the same volume as the sample of interest.

16. The method of claim 10 wherein the reference sample has an approximate impulse response.

17. The method of claim 10 wherein the reference sample is carbon black.

18. A method of performing photoacoustic spectroscopy on a sample of interest in a Fourier transform spectrometer, the method comprising, for at least one particular retardation value in the Fourier transform spectrometer:

using a piezoelectric transducer (PZT) to change the retardation value relative to the particular retardation value so as to illuminate the sample of interest with a pulse of analytic radiation, the pulse having a particular time dependence p(t);

detecting acoustic signals resulting from the pulse of analytic radiation encountering the sample using a detector system;

capturing a series of discrete values output from the detector system, the series of discrete values having a time dependence $o_S(t)$;

computing a Fourier transform $O_S$ of $o_S(t)$;

using a piezoelectric transducer (PZT) to change the retardation value relative to the particular retardation value so as to illuminate a reference sample with a pulse of analytic radiation, the pulse having the time dependence of p(t);

detecting acoustic signals resulting from the pulse of analytic radiation encountering the reference sample using the detector system;

capturing a series of discrete values output from the detector system, the series of discrete values having a time dependence $o_R(t)$;

computing a Fourier transform $O_R$ of $o_R(t)$;

computing an inverse Fourier transform of the ratio $O_S/O_R$ to provide a series of values $s(t_i)$ for a series of times $t_i$, the values $s(t_i)$ representing the impulse response s(t) of the sample of interest for that retardation value.

19. The method of claim 18 wherein the reference sample has the same volume as the sample of interest.

20. The method of claim 18 wherein the reference sample has an approximate impulse response.

21. The method of claim 18 wherein the reference sample is carbon black.

22. The method of claim 18 wherein said steps on the sample of interest and the reference sample are performed for each of a series of retardation values in the Fourier transform spectrometer.

23. The method of claim 22, and further comprising computing a spectrum for a particular time $t_k$ based on an interferogram having the respective values $s(t_k)$ for each of the N retardation values.

* * * * *